(12) United States Patent
Marash et al.

(10) Patent No.: US 11,076,816 B2
(45) Date of Patent: Aug. 3, 2021

(54) IMAGING SYSTEM AND METHOD

(71) Applicant: P-CURE, LTD., Lod (IL)

(72) Inventors: Michael Marash, Rishon Le'tzion (IL); Yigal Livne, Alfei Menashe (IL)

(73) Assignee: P-CURE LTD., Lod (IL)

( * ) Notice: Subject to any disclaimer, the term of this patent is extended or adjusted under 35 U.S.C. 154(b) by 525 days.

(21) Appl. No.: 15/748,187

(22) PCT Filed: Aug. 2, 2016

(86) PCT No.: PCT/IL2016/050844
§ 371 (c)(1),
(2) Date: Jan. 28, 2018

(87) PCT Pub. No.: WO2017/021962
PCT Pub. Date: Feb. 9, 2017

(65) Prior Publication Data
US 2018/0220975 A1 Aug. 9, 2018

Related U.S. Application Data

(60) Provisional application No. 62/200,038, filed on Aug. 2, 2015.

(51) Int. Cl.
*A61B 6/03* (2006.01)
*A61B 6/04* (2006.01)
(Continued)

(52) U.S. Cl.
CPC .............. *A61B 6/035* (2013.01); *A61B 6/032* (2013.01); *A61B 6/0478* (2013.01); *A61B 6/10* (2013.01);
(Continued)

(58) Field of Classification Search
CPC ...................................................... A61B 6/035
See application file for complete search history.

(56) References Cited

U.S. PATENT DOCUMENTS

| 5,396,535 A | 3/1995 | Linhart |
| 2005/0053186 A1 | 3/2005 | Sukovic et al. |
| (Continued) | | |

FOREIGN PATENT DOCUMENTS

| CN | 201227280 Y | 4/2009 |
| CN | 201328818 Y | 10/2009 |
| (Continued) | | |

OTHER PUBLICATIONS

International Search Report dated Nov. 8, 2016 by the European Patent Office for PCT/IL2016/050844.
(Continued)

*Primary Examiner* — Edwin C Gunberg
(74) *Attorney, Agent, or Firm* — The Roy Gross Law Firm, LLC; Roy Gross (57) ABSTRACT

An imaging system constituted of: an imager; an imager translation mechanism arranged to translate the imager along a predetermined translation axis in each of a first direction and a second direction responsive to a provided electrical power, the second direction opposing the first direction, the predetermined translation axis exhibiting an imaging angle with a floor, the first direction being toward the floor along the translation axis, the imaging angle being less than 90 degrees and greater than 0 degrees; a piston translation mechanism; and a piston power mechanism arranged to provide motive power to the piston translation mechanism, wherein the piston translation mechanism is arranged to translate the imager in the second direction responsive to the provided motive power in the absence of the provided electrical power.

20 Claims, 10 Drawing Sheets

(51) Int. Cl.
  *A61B 6/10* (2006.01)
  *A61B 6/00* (2006.01)
  *A61N 5/10* (2006.01)

(52) U.S. Cl.
  CPC ............ *A61B 6/447* (2013.01); *A61B 6/4429* (2013.01); *A61B 6/4447* (2013.01); *A61B 6/4476* (2013.01); *A61N 5/1049* (2013.01); *A61N 2005/1061* (2013.01); *A61N 2005/1063* (2013.01); *A61N 2005/1087* (2013.01)

(56) References Cited

U.S. PATENT DOCUMENTS

| 2008/0317216 A1 | 12/2008 | Lifshitz et al. |
| 2009/0190714 A1 | 7/2009 | Partain |
| 2011/0211665 A1 | 9/2011 | Maurer et al. |
| 2012/0324648 A1* | 12/2012 | Amano ................ A61B 6/037 5/601 |
| 2014/0098930 A1* | 4/2014 | Litzenberger ......... A61B 6/541 378/4 |
| 2015/0208992 A1 | 7/2015 | Marash et al. |

FOREIGN PATENT DOCUMENTS

| CN | 201642057 U | 11/2010 |
| CN | 102791198 A | 11/2012 |
| CN | 202821390 U | 3/2013 |
| CN | 203539367 U | 4/2014 |
| CN | 203977932 U | 12/2014 |
| WO | 2015100310 A1 | 7/2015 |

OTHER PUBLICATIONS

Written Opinion of the International Searching Authority dated Nov. 8, 2016 by the European Patent Office for PCT/IL2016/050844.

* cited by examiner

IMAGING SYSTEM AND METHOD

CROSS-REFERENCE TO RELATED APPLICATIONS

This application claims priority from U.S. provisional patent application Ser. 62/200,038, filed Aug. 2, 2015 and entitled "IMAGING SYSTEM AND METHOD", the entire contents of which are incorporated herein by reference.

TECHNICAL FIELD OF THE INVENTION

The invention relates generally to the field of imaging devices and in particular to an angled imaging system and method.

BACKGROUND OF THE INVENTION

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The charged protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

Irradiation treatment is performed on a target tissue in a well defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction.

Unfortunately, the necessary treatment position can be varied to a great degree, yet current CT imagers are limited in their degree of movement. Therefore, utilizing current CT imagers does not allow imaging a patient in the planned treatment position. Disadvantageously, a change in the position of the patient can cause a change in the position of one or more organs and/or tissues within the body. Thus, when the patient is imaged in a position restricted by the movement restrictions of the CT imager, the image may not accurately present the position of the target tissue when in the treatment position.

Additionally, at each fraction, care must be taken to ensure proper patient positioning, responsive to the placement markers, so as to avoid damage to organs in vicinity of the target tissue. Positioning of the patient responsive to the markers is typically performed based on visualization of the patient, responsive to the defined markers. Disadvantageously, positioning based on visualization is not always accurate. Imaging the patient prior to treatment, such as with a computed tomography (CT) imager, would be advantageous as it would provide more accurate positioning of the target tissue in relation to the irradiation treatment source. Unfortunately, as described above, utilizing current CT imagers does not allow imaging the patient in the planned treatment position and thus a shift may occur in the position of the patient during the movement from the imaging position in relation to the CT imager to the planned treatment position.

Although vertical CT imagers do exist to image a patient in a vertical position, i.e. standing up or sitting down, these vertical CT imagers provide several disadvantages. Firstly, the size of the CT imager typically does not allow for the entirety of a patient to be imaged when seated. Particularly, the distance between the back of the chair and the patient's knees is generally greater than the diameter of the opening of the CT imager. Typically, the diameter of the opening in the CT imager is about 85 cm, which is generally less than the distance between the back of the chair supporting the patient and the patient's knees. Secondly, a patient seated in an upright position generally does not support themselves very well and as a result shifts in position of the patient are expected. Therefore, the position in which the patient is to be treated may not be the same position in which the patient was imaged. Thirdly, in case of a power shortage, or a motor malfunction, when the patient is inside the CT imager, extracting the patient from within the CT imager can be complicated and dangerous.

U.S. patent application publication S/N US 2015/0208992, published Jul. 30, 2015 to Marash et al. and entitled "APPARATUS AND METHOD FOR PROVIDING PATIENT IMAGING", the entire contents of which are incorporated herein by reference, teaches a system for imaging a patient at an angle. However, the provided system exhibits a complicated mechanism for extending the imager along an imaging axis. Additionally, in case of a power shortage or motor malfunction extracting the patient from within the CT imager is complicated.

SUMMARY OF THE INVENTION

Accordingly, it is a principal object of the present invention to overcome disadvantages of prior art methods and arrangements of patient imaging. In one embodiment, an imaging system is provided, the imaging system comprising: an imager; an imager translation mechanism arranged to translate the imager along a predetermined translation axis in each of a first direction and a second direction responsive to a provided electrical power, the second direction opposing the first direction, the predetermined translation axis exhibiting an imaging angle with a floor, the first direction being toward the floor along the translation axis, the imaging angle being less than 90 degrees and greater than 0 degrees; a piston translation mechanism; and a piston power mechanism arranged to provide motive power to the piston translation mechanism, wherein the piston translation mechanism is arranged to translate the imager in the second direction responsive to the provided motive power in the absence of the provided electrical power.

In one embodiment, the system further comprises a counterweight arranged to translate along a counterweight axis, the counterweight arranged to provide counterbalance to the imager, wherein the arrangement of the piston translation mechanism to translate the imager in the second direction comprises translating the counterweight along the counterweight axis. In another embodiment, the piston translation mechanism is further arranged to provide counterbalance to the imager.

In one embodiment, the imager translation mechanism comprises: a screw; and a motor, the motor arranged to rotate the screw, the translation of the imager along the translation axis responsive to the screw rotation, wherein the provided motive power comprises hydraulic power. In another embodiment, the imaging angle is between 55-85 degrees. In one further embodiment, the imaging angle is between 65-75 degrees.

In one embodiment, the imager comprises a CT imager.

In one independent embodiment, an imaging method is provided, the method comprising: providing an imager; providing an imager translation mechanism arranged to translate the imager along a predetermined translation axis in each of a first direction and a second direction responsive to a provided electrical power, the second direction opposing the first direction, the predetermined translation axis exhibiting an imaging angle with a floor, the first direction being toward the floor along the translation axis, the imaging angle being less than 90 degrees and greater than 0 degrees; providing a piston translation mechanism; and providing motive power to the provided piston translation mechanism, wherein the provided piston translation mechanism is arranged to translate the imager in the second direction responsive to the provided motive power in the absence of the provided electrical power.

In one embodiment, the method further comprises providing a counterweight arranged to translate along a counterweight axis, the provided counterweight arranged to provide counterbalance to the provided imager, wherein the arrangement of the provided piston translation mechanism to translate the provided imager in the second direction comprises translating the provided counterweight along the counterweight axis. In another embodiment, the provided piston translation mechanism is further arranged to provide counterbalance to the provided imager.

In one embodiment, the provided imager translation mechanism comprises a screw, wherein the method further comprises rotating the screw, the translation of the provided imager along the translation axis responsive to the screw rotation, and wherein the provided motive power comprises hydraulic power. In another embodiment, the imaging angle is between 55-85 degrees. In one further embodiment, the imaging angle is between 65-75 degrees.

In one embodiment, the provided imager comprises a computer tomography (CT) imager.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1A:
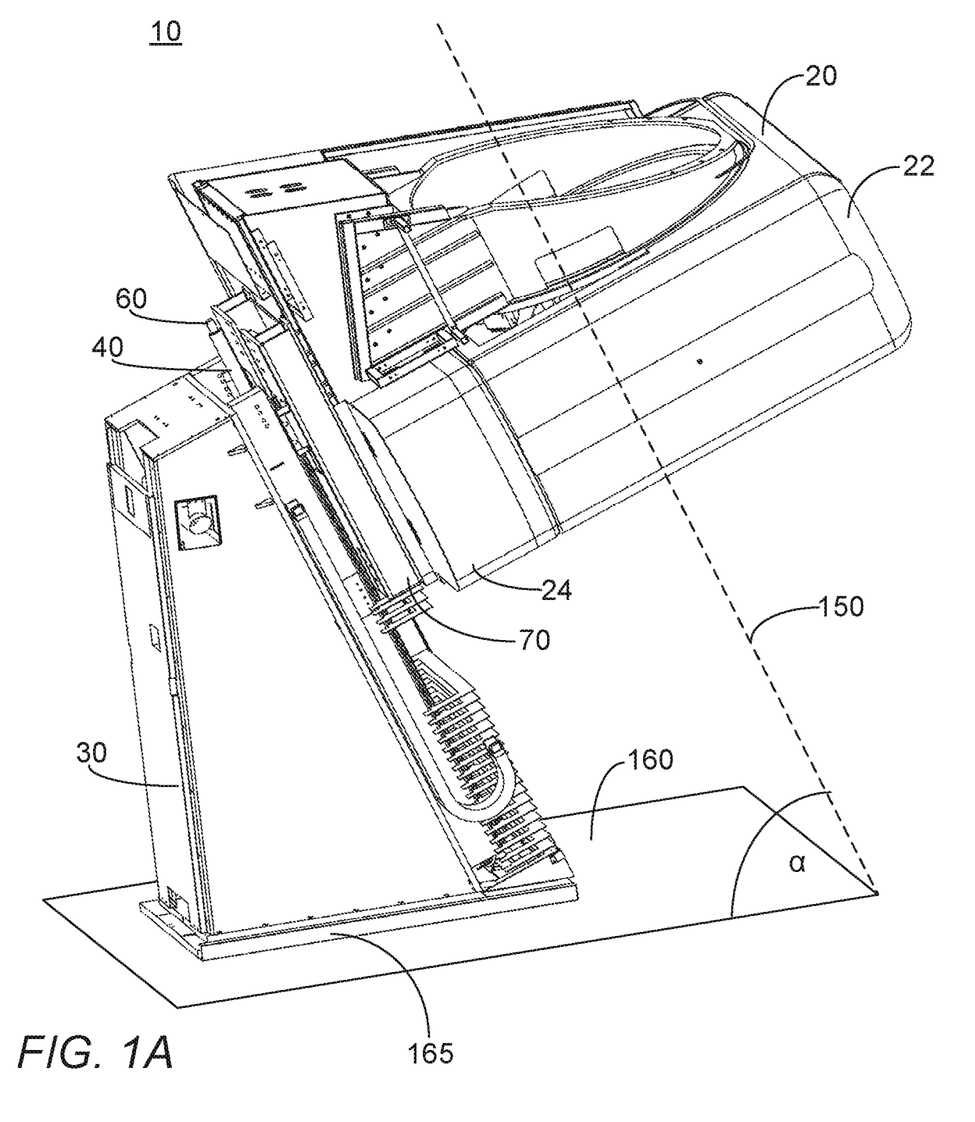
FIGS. 1A-1D illustrate various high level views of a first embodiment of an imager translation apparatus, according to certain embodiments.
Figure 1B:
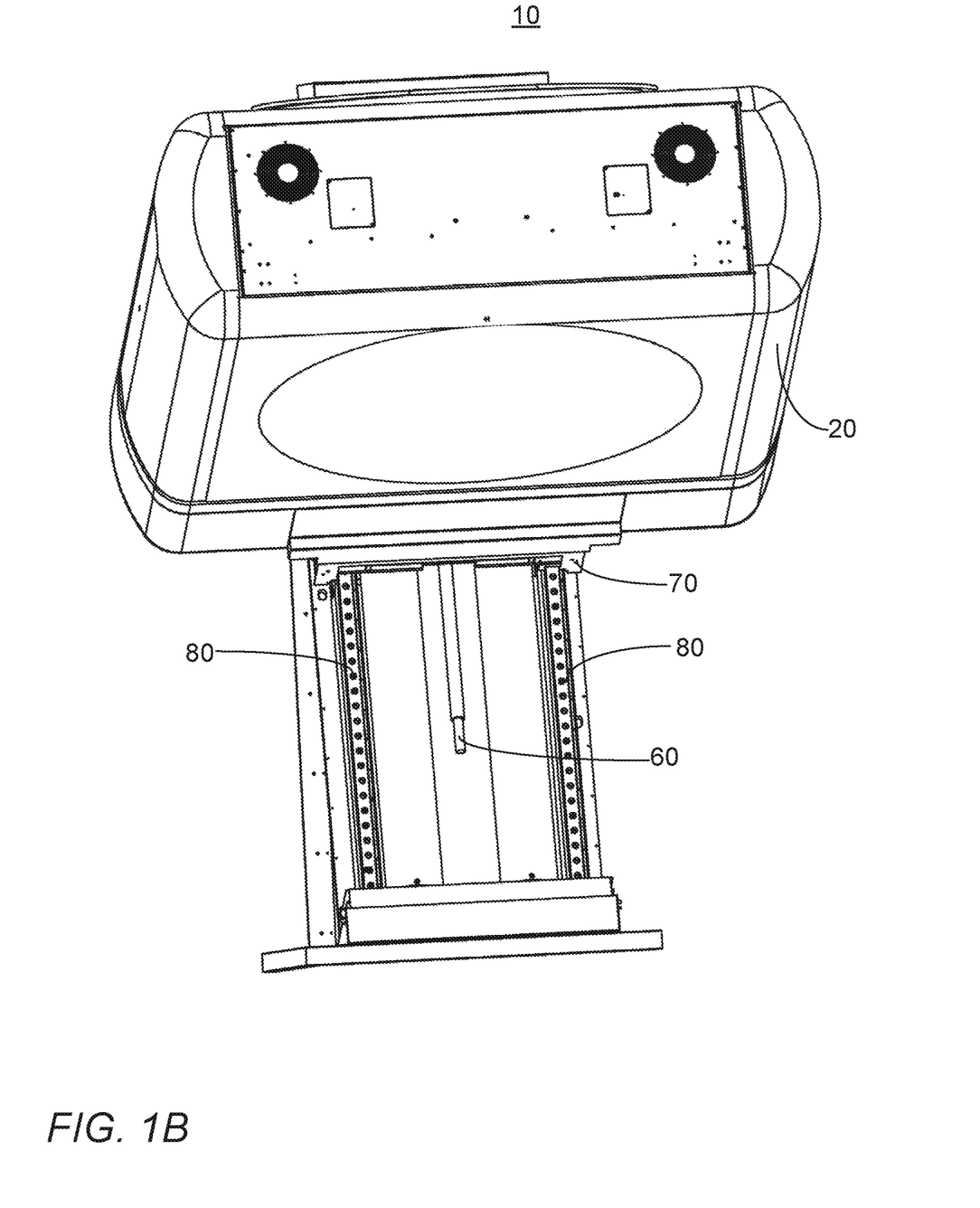
Figure 1C:
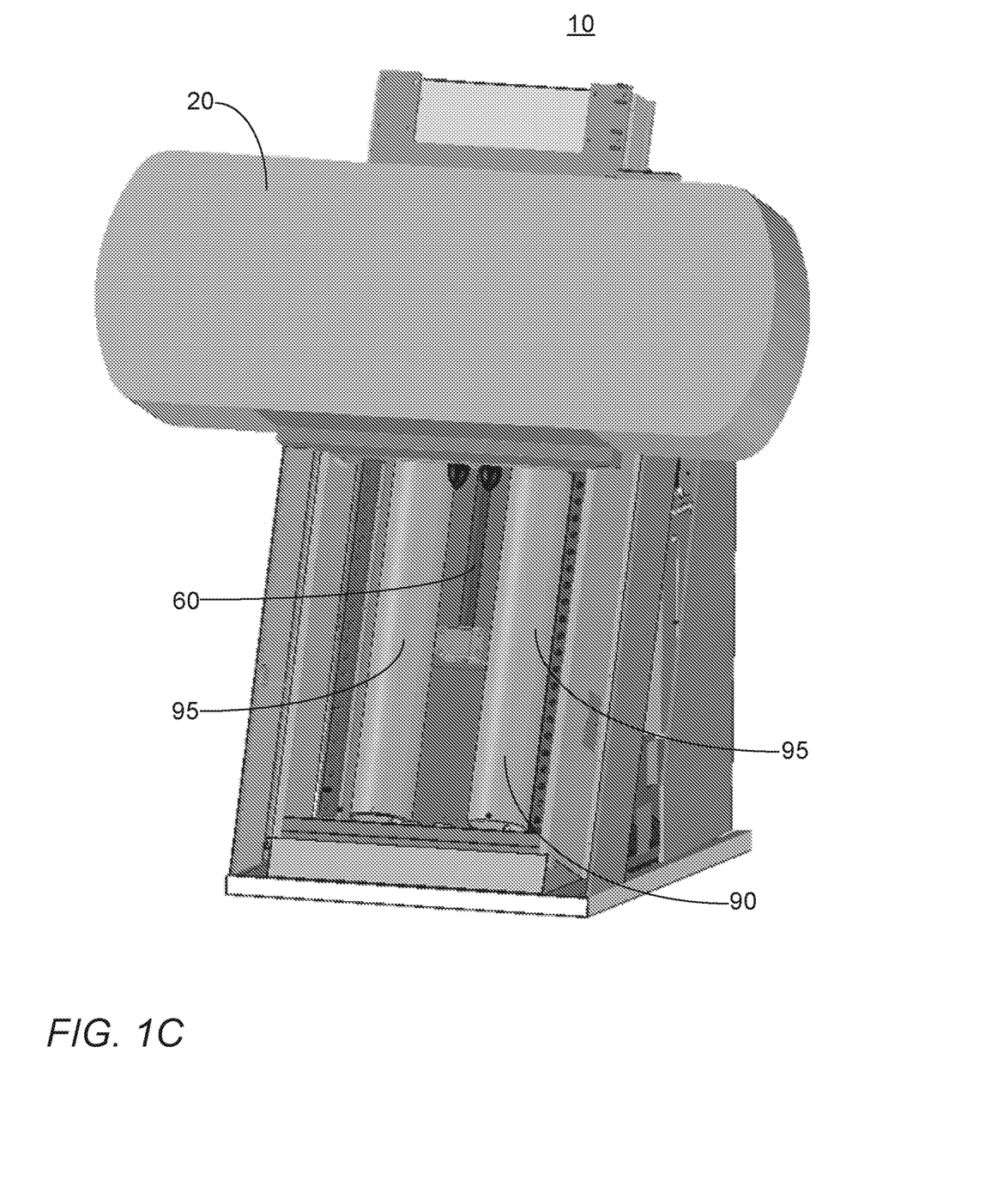
Figure 1D:
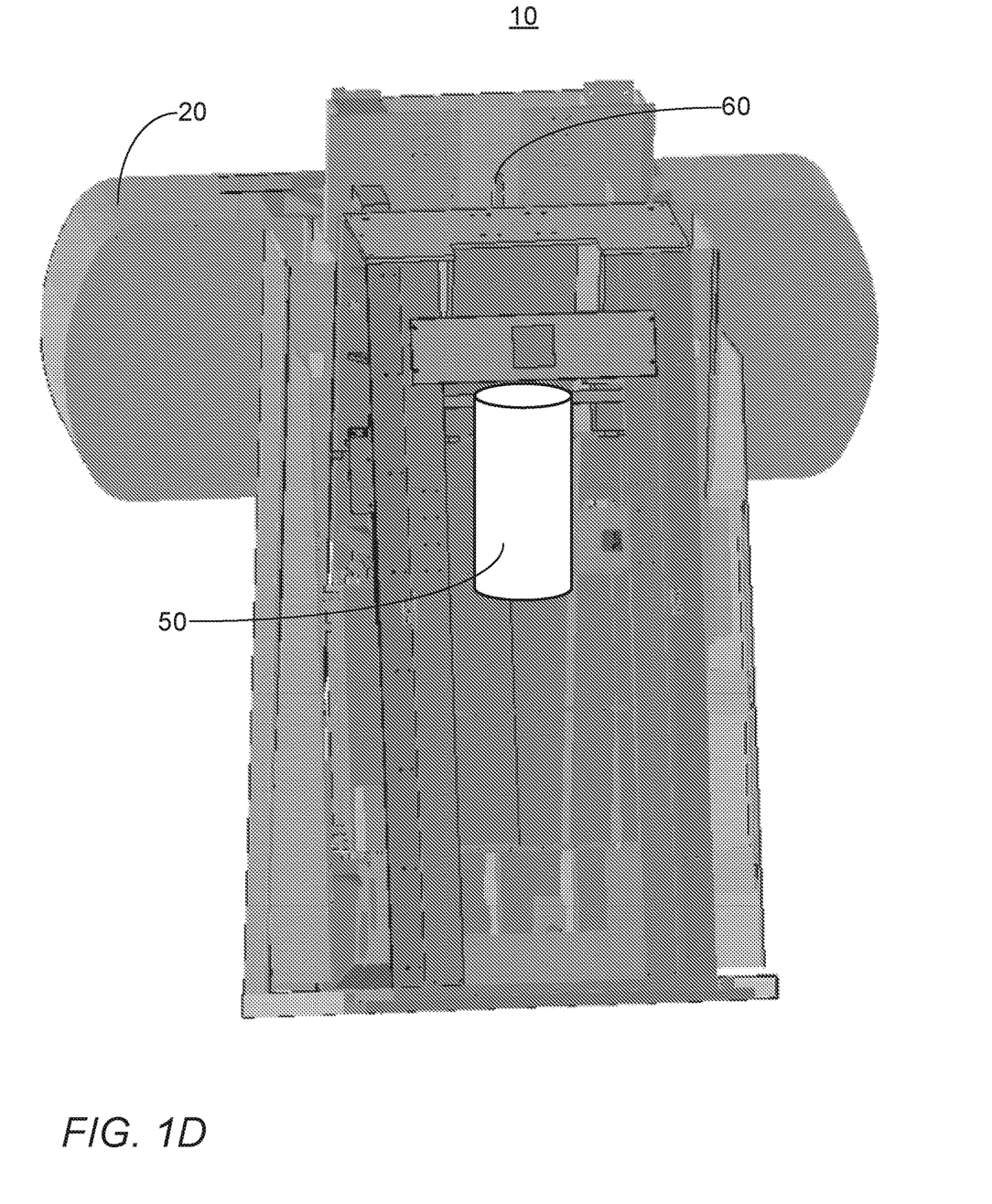

FIGS. 1A-1F illustrate various high level view of an imaging system 10 comprising: an imager 20, exhibiting a front end 22 and a back end 24; and an imager translation apparatus 30. Particularly, FIG. 1A illustrates a high level side view of imaging system 10. FIG. 1B illustrates a high level front view of imaging system 10. FIG. 1C. illustrates a more detailed high level front view of imaging system 10. FIG. 1D. illustrates a high level rear view of imaging system 10. FIGS. 1A-1D will be described together.

In one particular embodiment, imager 20 comprises a CT imager. Imager translation apparatus 30 comprises: an imager translation mechanism 40 comprising a motor 50 and a screw 60; a platform 70; a pair of rails 80; and a piston translation mechanism 90. Piston translation mechanism 90 comprises a pair of hydraulic pistons 95.

Imager 20 is positioned on, and secured to, platform 70. Platform 70 is positioned over rails 80 and is arranged to slide thereover. Screw 60 is coupled to both motor 50 and platform 70 such that motor 50 is arranged to turn screw 60 and platform 70 is arranged to be translated along screw 60 in a worm drive configuration. Although imager translation mechanism 40 is described herein in a worm drive configuration, this is not meant to be limiting in any way and any type of translation mechanism can be implemented without exceeding the scope. In one embodiment (not shown), hydraulic imager translation mechanism 90 further comprises a hydraulics liquid reservoir, a pressure sensor and an electric hydraulic pump, as will be described below. As illustrated, imager translation apparatus 30 is positioned on floor 160, a base 165 of imager translation apparatus 30 in contact with floor 160. Imager translation apparatus 30 extends generally upwards from base 165. In one non-limiting embodiment, imager translation apparatus 30 exhibits a generally right triangle shape with rails 80 extending along the hypotenuse thereof.

In operation, motor 50 is arranged to turn screw 60. As screw 60 turns, platform 70 is translated therealong. Since imager 20 is secured to platform 70, imager 20 is translated along a translation axis 150, responsive to the operation of motor 50 and screw 60. Translation axis 150 exhibits an acute imaging angle, denoted a, with the floor 160 of a room which contains therein imaging system 10. In one further embodiment, imaging angle α between translation axis 150 and floor 160 is between 55-85 degrees, such that the pelvis of a patient who is seated in an inclination of between 5-35 degrees can be imaged by imager 20. Particularly, due to imaging angle α, front end 22 of imager 20 is higher than back end 24 thereof. As a result, imager 20 is able to extend farther along the patient's body and cover the pelvis area before front end 22 thereof hits the patient's knees. Optionally, imaging angle α is between 65-75 degrees such that the pelvis of a patient seated in an inclination of between 15-25 degrees can imaged by imager 20. Additionally, when the patient is seated in an incline, preferably of about 20 degrees, the position is more comfortable than when seated in a vertical position and movement of the patient is less likely.

When screw 60 turns in a first direction, imager 20 is translated along translation axis 150 towards floor 160. When screw 60 turns in a second direction, opposing the first direction, imager 20 is translated along translation axis 150 away from floor 160.

In one embodiment, hydraulic pistons 95 act as a counterbalance for motor 50 and screw 60, as known to those skilled in the art at the time of the invention. Particularly, the electric hydraulic pump (not shown) is arranged to adjust the liquid flow from the associated hydraulic reservoir so as to maintain a constant pressure at hydraulic pistons 95, responsive to the pressure sensor.

In the event of a power outage, or any type of problem with the operation of motor 50, a piston power mechanism (not shown) is arranged to provide motive power, specifically hydraulic power, to hydraulic pistons 95. Responsive to the provided hydraulic power, hydraulic pistons 95 are arranged to extend thereby pushing platform 70 along rails 80 away from floor 160. As a result, imager 20 is translated along translation axis 150 away from floor 160 and away from the patient which is being imaged. The patient can thus exit the chair and not get stuck by image 20.

Figure 2A:
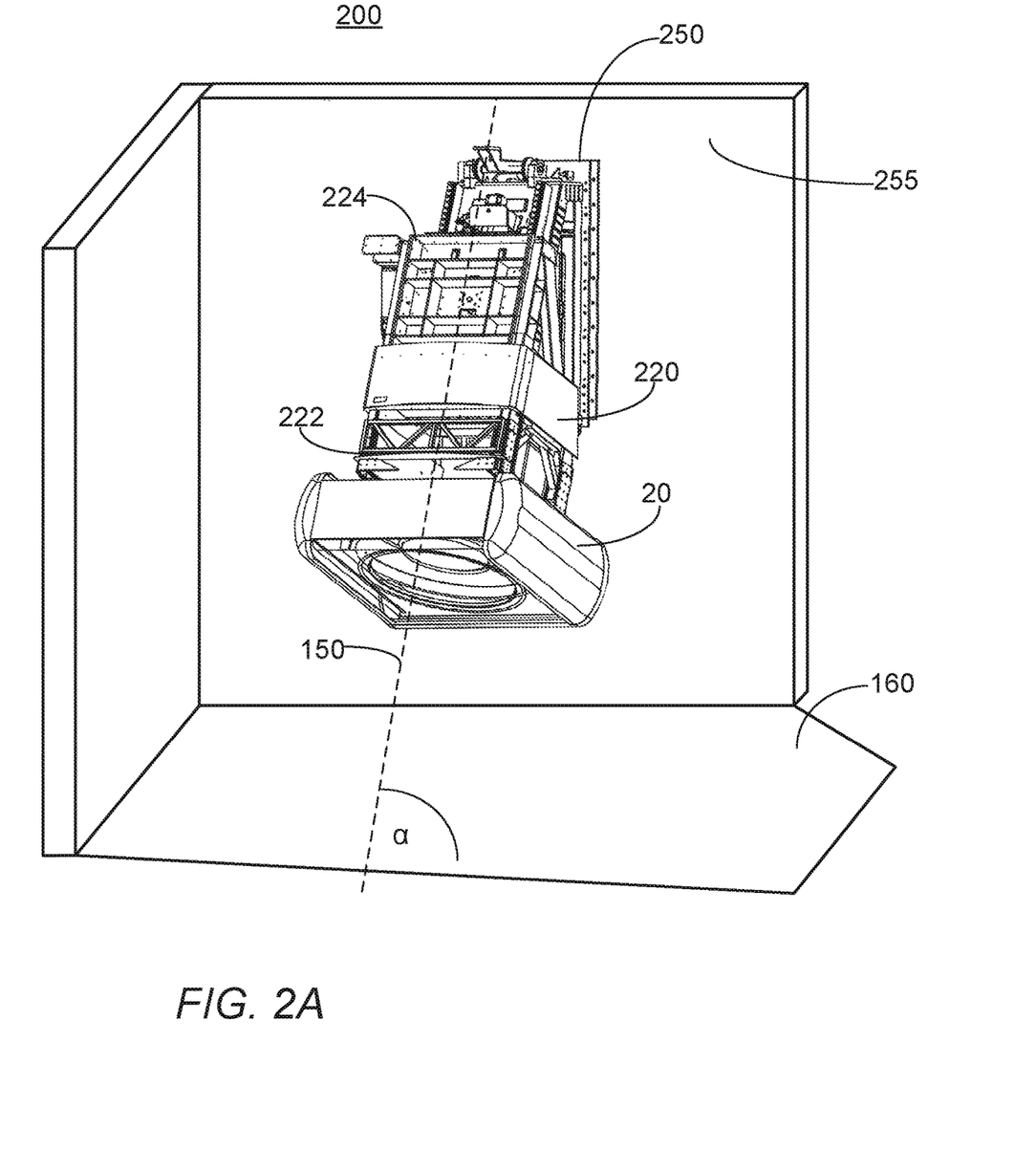
FIGS. 2A-2F illustrate various high level views of a second embodiment of an imager translation apparatus, according to certain embodiments.
Figure 2B:
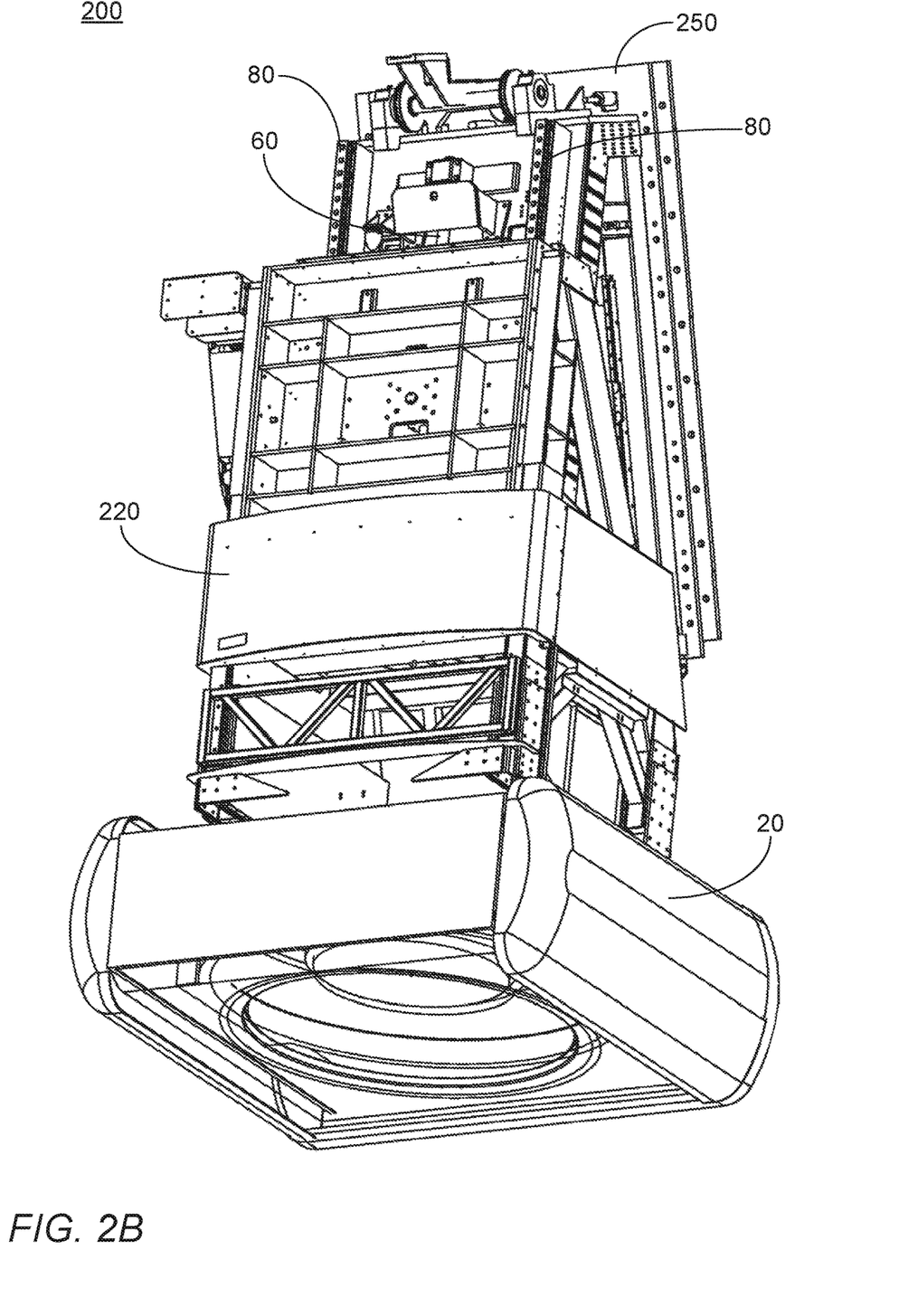
Figure 2C:
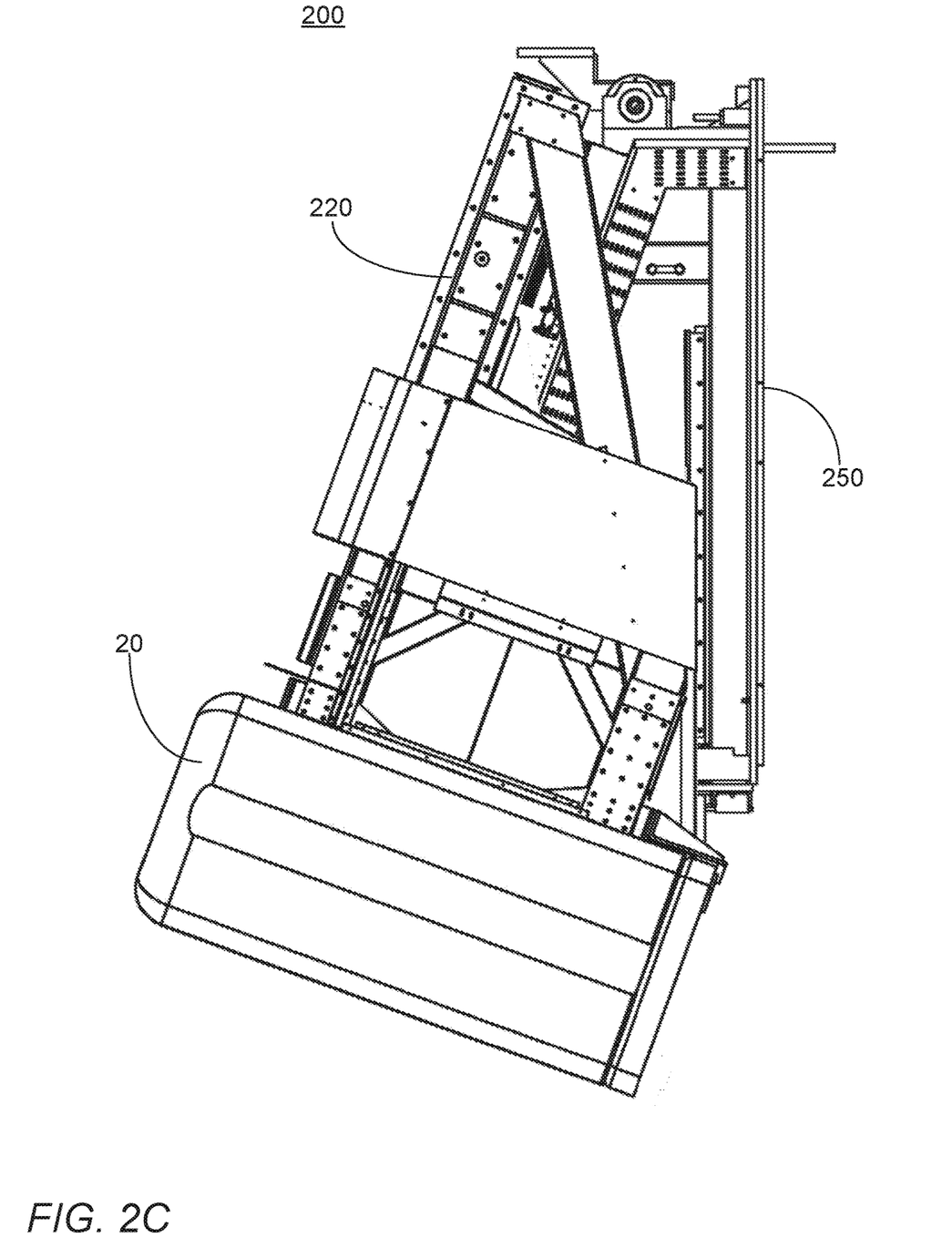
Figure 2D:
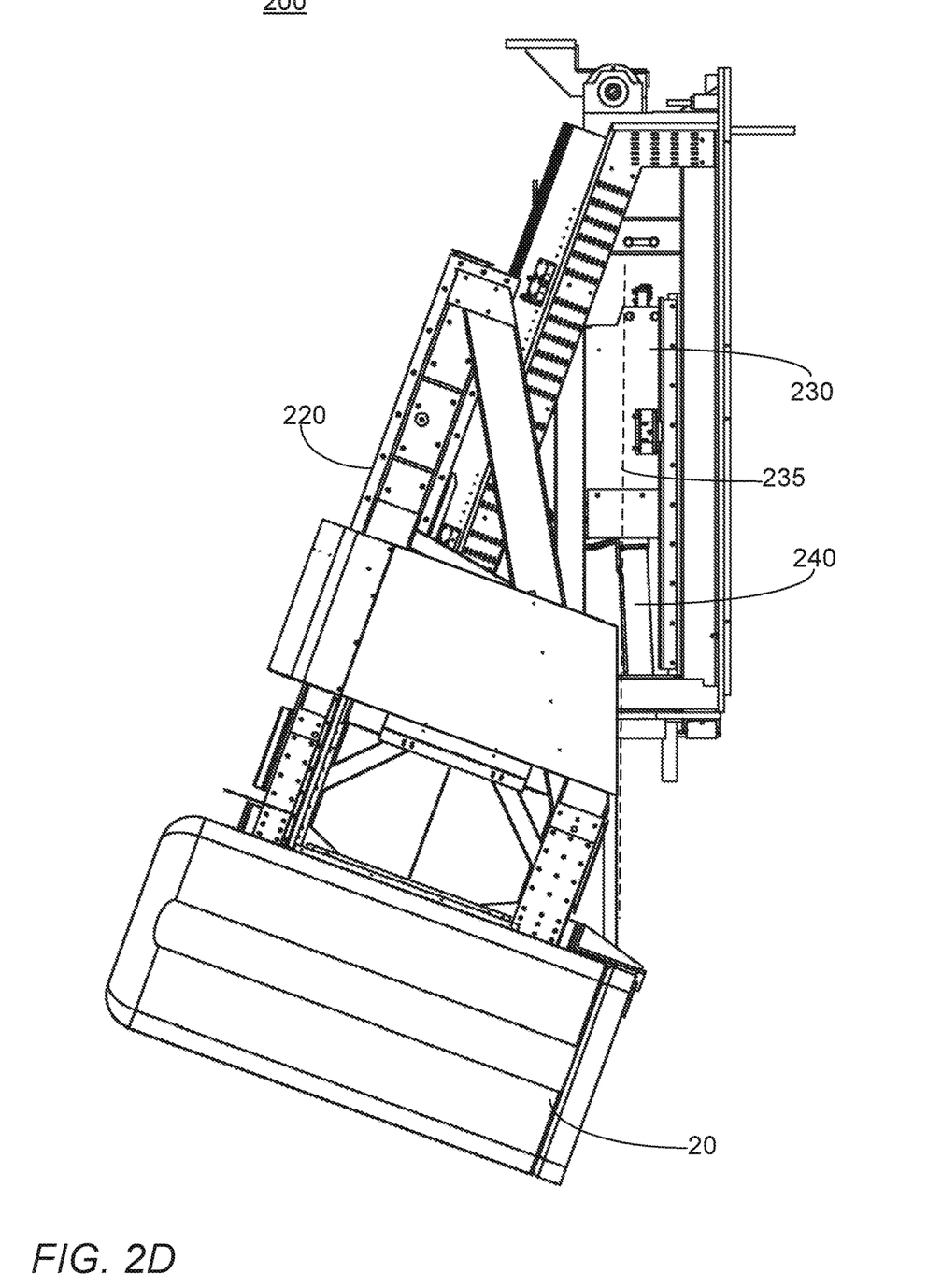
Figure 2E:
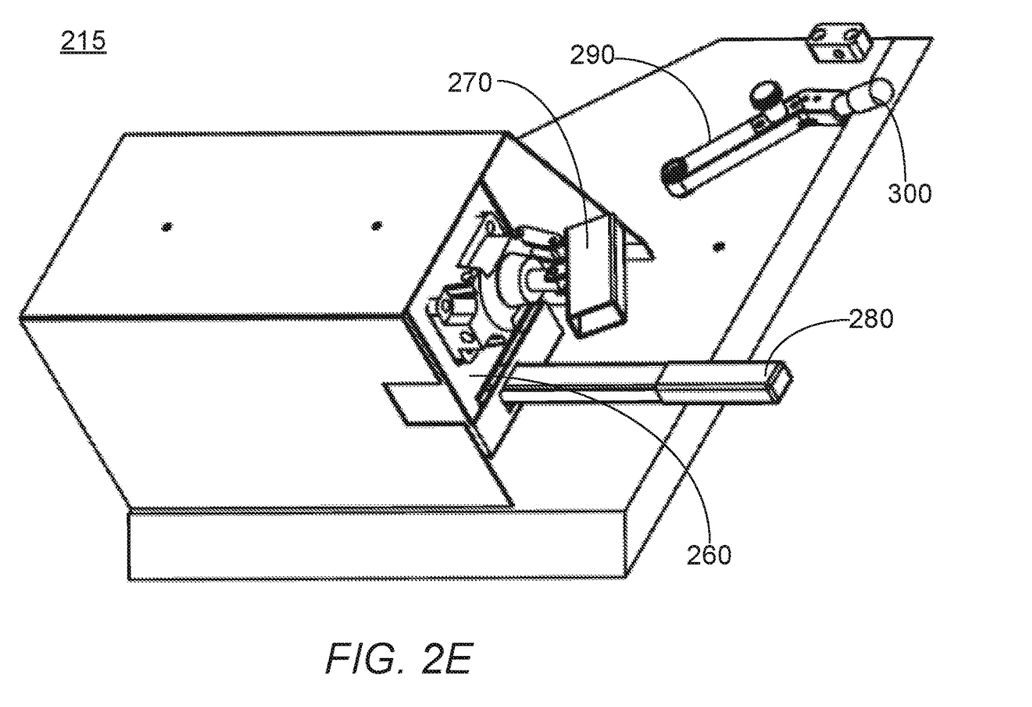
Figure 2F:
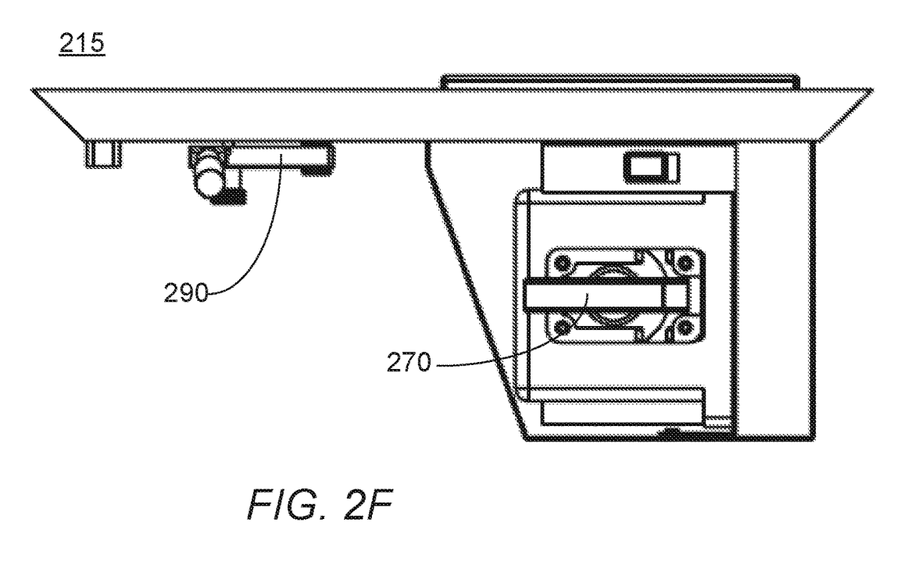

FIGS. 2A-2E illustrate various high level views of an imaging system 200, imaging system 200 comprising: an imager 20; an imager translation apparatus 210; and a piston power mechanism 215. Particularly, FIG. 2A illustrates a first high level perspective view of imager 20 and imager translation apparatus 210. FIG. 2B illustrates a second high level perspective view of imager 20 and imager translation apparatus 210. FIG. 2C illustrates a high level side view of imager 20 and imager translation apparatus 210 in a retracted position. FIG. 2D illustrates a high level perspective side view of imager 20 and imager translation apparatus 210 in an extended position. FIG. 2E illustrates a high level perspective view of piston power mechanism 215. FIG. 2F illustrates a high level side view of piston power mechanism 215. FIGS. 2A-2F are described together.

Imager translation apparatus 210 comprises: a pair of rails 80; an extension unit 220; a screw 60; a motor (not shown); a counterweight 230; a piston translation mechanism comprising a piston 240; and a wall attachment unit 250. Imager 20 is positioned on, and secured to, a first end 222 of extension unit 220. Counterweight 230 is coupled to a second end 224 of extension unit 220 via a cable (not shown). A first end of piston 240 is positioned inside of counterweight 230 and second end of piston 240 is coupled to wall attachment unit 250. First end 222 of extension unit 220 opposes second end 224 of extension unit 220. Extension unit 220 is positioned on rails 80 and screw 60 extends through extension unit 220, extension unit 220 arranged to be translated along screw 60 responsive to the rotation thereof. Rails 80 are positioned on wall attachment unit 250 and wall attachment unit 250 is secured to a wall 255 of the room containing imaging system 200 with second end 224 of extension unit 220 facing wall 255.

Piston power mechanism 215 comprises: a hydraulic liquid reservoir 260; a manual hydraulic pump 270; a movable pump handle 280; and a manual break release 290. In one embodiment, manual break release 290 comprises a break release handle 300 and a cable (not shown).

In operation, as described above in relation to platform 70, extension unit 220 is translated over rails 80 responsive to the motor turning screw 60. Responsive to the translation of extension unit 220 over rails 80, imager 20 is likewise translated along a translation axis 150. As described above in relation to imaging system 10, in one embodiment translation axis 150 exhibits an acute angle with floor 160, optionally an angle between 55-85 degrees, further optionally between 65-75 degrees. Extension unit 220 and imager 20 are counterbalanced by counterweight 230. Particularly, when imager 20 is translated along translation axis 150 towards a floor 160, counterweight 230 is pulled upwards along a counterweight axis 235, the mass of counterweight 230 providing counterbalance to imager 20. When imager 20 20 is translated along translation axis 150 away from floor 160, and towards wall 255, counterweight 230 is drops down counterweight axis 235 responsive to gravity. In one embodiment, counterweight axis 235 exhibits a right angle with floor 160.

When electric power is provided to the motor rotating screw 60, piston 240 extends and retracts responsive to the movement of counterweight 230 along counterweight axis 235. In the event of a power shortage, or any problem with the motor, piston power mechanism 215 is arranged to provide motive power to piston 240. In one preferred embodiment, piston 240 is a hydraulic piston and piston power mechanism 215 is arranged to provide hydraulic power to piston 240. This allows piston 240 to retract, thereby pulling counterweight 230 down counterweight axis 235. As a result, imager 20 is pulled along translation axis 150 away from floor 160, thereby avoiding trapping a patient within imager 20.

Particularly, movable pump handle 280 is inserted into manual hydraulic pump 270. A user holding movable pump handle 280 can then manually pump manual hydraulic pump 270. The pumping action of the user provides hydraulic energy to piston 240, via hydraulic liquid reservoir 260, to pull counterweight 230 down counterweight axis 235, as described above. In one embodiment, hydraulic liquid reservoir 260 is not separately provided and manual hydraulic pump 270 is arranged to utilize the hydraulic liquid from a hydraulic liquid reservoir of piston 240 to provide hydraulic energy to piston 240 for translating counterweight 230 and imager 20.

When power is not being supplied, an emergency brake (not shown) is applied to extension unit 220 so it won't slide all the way down rails 80. Prior to operating manual hydraulic pump 270, the emergency brake is released via manual break release 290. Particularly, a user pulls break release handle 300 from a first position to a second position. When being moved to the second position, break release handle 300 pulls on the associated cable, which is also coupled to the emergency break. As a result, the tension of the cable increases thereby pulling on the emergency break and allowing extension unit 220 to be translated along rails 80. Preferably, break release handle 300 is then secured to the second position.

Figure 3:
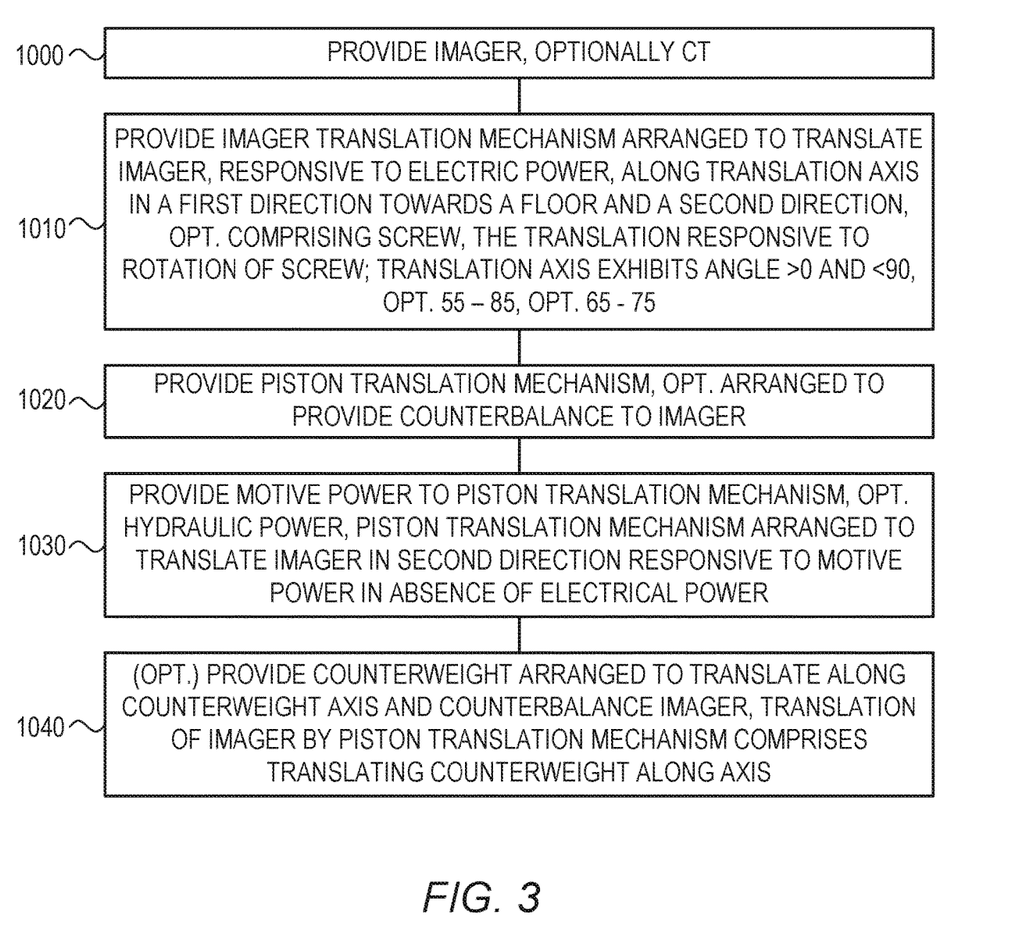
FIG. 3 illustrates a high level flow chart of an imager translation method, according to certain embodiments.

FIG. 3 illustrates a high level flow chart of an imager translation method. In stage 1000 an imager is provided, optionally a CT imager. In stage 1010, an imager translation mechanism is provided. Responsive to a provided electric power, the imager translation mechanism arranged to translate the imager of stage 1000 along a predetermined translation axis in each of a first direction and a second direction responsive to a provided electrical power, the second direction opposing the first direction. The predetermined translation axis exhibits an imaging angle with a floor, the first direction being toward the floor along the translation axis. Additionally, the imaging angle is an acute angle of less than 90 degrees and greater than 0 degrees, optionally between 55-85 degrees, further optionally between 65-75 degrees. Optionally, the imager translation mechanism comprises a screw, the translation of the imager along the translation axis responsive to a rotation of the screw by an electrically driven motor. Particularly, responsive to rotation of the screw in a first rotational direction, the imager is translated along the translation axis in the first direction. Responsive to rotation of the screw in a second rotation direction, the imager is translated along the translation axis in the second direction.

In stage 1020, a piston translation mechanism is provided. Optionally, the piston translation mechanism comprises one or more hydraulic pistons. Optionally, the piston translation mechanism is arranged to provide counterbalance to the imager of stage 1000.

In stage 1030, motive power is provided to the piston translation mechanism of stage 1020, the motive power optionally being hydraulic power. The piston translation is arranged to translate the imager of stage 1000 in the second direction responsive to the provided motive power in the absence of the provided electrical power.

In optional stage 1040, a counterweight is provided, the counterweight arranged to translate along a counterweight axis, the provided counterweight arranged to provide counterbalance to the provided imager. The arrangement of stage 1030, of the provided piston translation mechanism to translate the provided imager in the second direction, comprises translating the provided counterweight along the counterweight axis.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. An imaging system comprising:
   an imager;
   an imager translation mechanism arranged to translate said imager along a predetermined translation axis in each of a first direction and a second direction responsive to a provided electrical power, said second direction opposing said first direction, said predetermined translation axis exhibiting an imaging angle with a floor, said first direction being toward the floor along said translation axis, said imaging angle being less than 90 degrees and greater than 0 degrees;
   a piston translation mechanism; and
   a piston power mechanism arranged to provide motive power to said piston translation mechanism,
   wherein said piston translation mechanism is arranged to translate said imager in said second direction responsive to said provided motive power in the absence of the provided electrical power.

2. The system of claim 1, further comprising a counterweight arranged to translate along a counterweight axis, said counterweight arranged to provide counterbalance to said imager,
   wherein said arrangement of said piston translation mechanism to translate said imager in said second direction comprises translating said counterweight along said counterweight axis.

3. The system of claim 2, wherein said imager translation mechanism comprises:
   a screw; and
   a motor, said motor arranged to rotate said screw, said translation of said imager along said translation axis responsive to said screw rotation,
   wherein said provided motive power comprises hydraulic power.

4. The system of claim 2, wherein said imaging angle is between 55-85 degrees.

5. The system of claim 1, wherein said piston translation mechanism is further arranged to provide counterbalance to said imager.

6. The system of claim 5, wherein said imager translation mechanism comprises:
   a screw; and
   a motor, said motor arranged to rotate said screw, said translation of said imager along said translation axis responsive to said screw rotation,
   wherein said provided motive power comprises hydraulic power.

7. The system of claim 1, wherein said imaging angle is between 55-85 degrees.

8. The system of claim 7, wherein said imaging angle is between 65-75 degrees.

9. The system of claim 1, wherein said imager comprises a computer tomography (CT) imager.

10. The system of claim 1, wherein said imager translation mechanism comprises:
   a screw; and
   a motor, said motor arranged to rotate said screw, said translation of said imager along said translation axis responsive to said screw rotation,
   wherein said provided motive power comprises hydraulic power.

11. An imaging method, the method comprising:
   providing an imager;
   providing an imager translation mechanism arranged to translate said imager along a predetermined translation axis in each of a first direction and a second direction responsive to a provided electrical power, said second direction opposing said first direction, said predetermined translation axis exhibiting an imaging angle with a floor, said first direction being toward the floor along said translation axis, said imaging angle being less than 90 degrees and greater than 0 degrees;
   providing a piston translation mechanism; and
   providing motive power to said provided piston translation mechanism,
   wherein said provided piston translation mechanism is arranged to translate said imager in said second direction responsive to said provided motive power in the absence of the provided electrical power.

12. The method of claim 11, further comprising providing a counterweight arranged to translate along a counterweight axis, said provided counterweight arranged to provide counterbalance to said provided imager,
   wherein said arrangement of said provided piston translation mechanism to translate said provided imager in said second direction comprises translating said provided counterweight along said counterweight axis.

13. The method of claim 12, wherein said provided imager translation mechanism comprises a screw,
   wherein the method further comprises rotating said screw, said translation of said provided imager along said translation axis responsive to said screw rotation, and
   wherein said provided motive power comprises hydraulic power.

14. The method of claim 12, wherein said imaging angle is between 55-85 degrees.

15. The method of claim 11, wherein said provided piston translation mechanism is further arranged to provide counterbalance to said provided imager.

16. The method of claim 15, wherein said provided imager translation mechanism comprises a screw,
   wherein the method further comprises rotating said screw, said translation of said provided imager along said translation axis responsive to said screw rotation, and
   wherein said provided motive power comprises hydraulic power.

17. The method of claim 11, wherein said provided imager translation mechanism comprises a screw,
   wherein the method further comprises rotating said screw, said translation of said provided imager along said translation axis responsive to said screw rotation, and
   wherein said provided motive power comprises hydraulic power.

18. The method of claim 11, wherein said imaging angle is between 55-85 degrees.

19. The method of claim 18, wherein said imaging angle is between 65-75 degrees.

20. The method of claim 11, wherein said provided imager comprises a computer tomography (CT) imager.

* * * * *